United States Patent [19]

Hammerslag

[11] Patent Number: 5,529,577
[45] Date of Patent: Jun. 25, 1996

[54] SURFACE OPENING ADHESIVE SEALER

[75] Inventor: Julius G. Hammerslag, San Juan Capistrano, Calif.

[73] Assignee: Hemodynamics, Inc., San Clemente, Calif.

[21] Appl. No.: 278,728

[22] Filed: Jul. 21, 1994

Related U.S. Application Data

[63] Continuation of Ser. No. 127,769, Sep. 28, 1993, abandoned.

[51] Int. Cl.⁶ ..................................................... A61B 17/00
[52] U.S. Cl. ........................... 606/214; 606/213; 222/510; 401/263; 604/310; 604/183
[58] Field of Search ..................................... 606/212–214, 606/117, 92–95; 604/310, 311, 208, 210, 183; 222/510; 401/263

[56] References Cited

U.S. PATENT DOCUMENTS

| | | | |
|---|---|---|---|
| 55,008 | 3/1866 | Gannett | 222/510 |
| 1,071,063 | 8/1913 | Lee | 222/510 |
| 1,083,532 | 1/1914 | Grayham | 222/510 |
| 1,577,465 | 3/1926 | Houge | 401/263 |
| 2,012,164 | 8/1935 | Gordon | 222/510 |
| 2,388,321 | 11/1945 | Gereke | 604/311 |
| 2,636,647 | 4/1953 | Covitt et al. | 222/510 |
| 2,752,920 | 7/1956 | Kurkijian . | |
| 3,220,413 | 11/1965 | Sunnen . | |
| 3,223,083 | 12/1965 | Cobey . | |
| 3,527,841 | 9/1970 | Wicker, Jr. et al. . | |
| 3,559,652 | 2/1971 | Banitt et al. . | |
| 3,577,516 | 5/1971 | Gould et al. . | |
| 3,772,599 | 3/1973 | Robertson et al. . | |
| 4,578,055 | 3/1986 | Fischer | 604/311 |
| 4,981,483 | 1/1991 | Akimova et al. . | |
| 4,993,948 | 2/1991 | Cameron et al. | 604/311 |
| 5,011,493 | 4/1991 | Belykh et al. . | |
| 5,201,712 | 4/1993 | Bryant | 604/256 |
| 5,209,776 | 5/1993 | Bass et al. . | |
| 5,222,939 | 6/1993 | Tiefenbrun | 604/59 |
| 5,320,639 | 6/1994 | Rudnick | 606/213 |
| 5,324,305 | 6/1994 | Kanner | 606/213 |
| 5,383,897 | 1/1995 | Wholey | 606/213 |
| 5,838,896 | 1/1995 | Gershony et al. | 606/213 |

FOREIGN PATENT DOCUMENTS

| | | |
|---|---|---|
| WO/91/07136 | 3/1991 | WIPO ..................................... 606/153 |
| WO/9221297 | 12/1992 | WIPO . |
| WO/9306878 | 4/1993 | WIPO . |
| WO/9308746 | 5/1993 | WIPO . |

OTHER PUBLICATIONS

*Long Term Pathological Follow–Up of Cerebral Arteriovenous Malformations Treated by Embolization with Bucrylate,* by Harry V. Vinters et al., The New England Journal of Medicine, Feb. 29, 1986 pp. 477–483.

*Primary Examiner*—Stephen C. Pellegrino
*Assistant Examiner*—Jeffrey Schmidt
*Attorney, Agent, or Firm*—Knobbe, Martens, Olson & Bear

[57] ABSTRACT

Disclosed is a device for delivering tissue adhesives to a surface which covers or surrounds a lumen, cavity or organ, or potential lumen or cavity, within a human or animal. Also disclosed is a method of delivering tissue adhesives to a surface which covers or surrounds a lumen, cavity or organ, or potential lumen or cavity, within a human or animal. The method is particularly suited to sealing perforations in vascular walls, such as after arterial access for Percutaneous Transluminal Coronary Angioplasty (PTCA), Percutaneous Coronary Angiography and Percutaneous Coronary Atherectomy and similar diagnostic and therapeutic procedures.

8 Claims, 2 Drawing Sheets

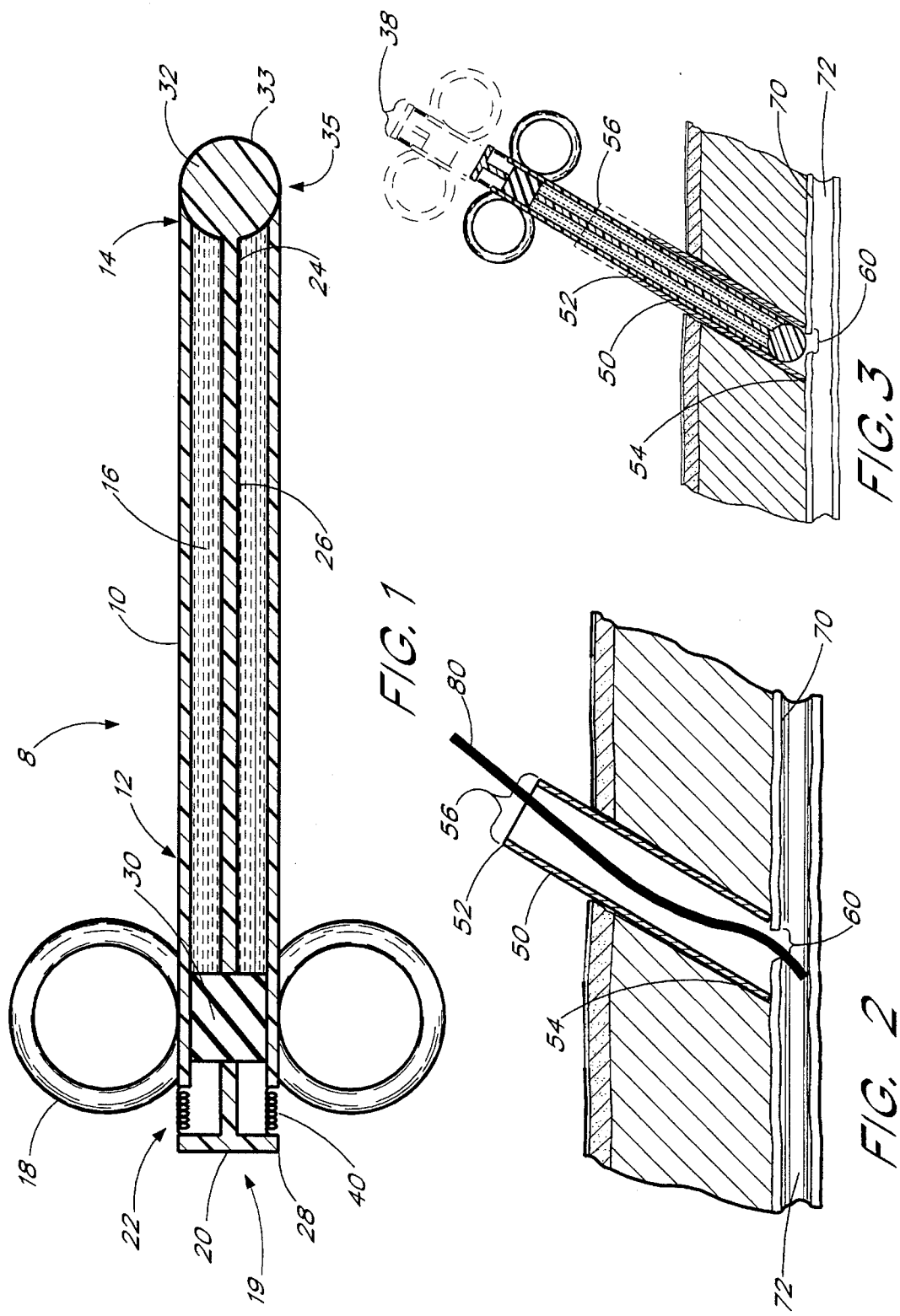

SURFACE OPENING ADHESIVE SEALER

This application is a continuation of application Ser. No. 08/127,769, filed Sep. 28, 1993, now abandoned.

FIELD OF THE INVENTION

This invention relates to methods and devices for delivering tissue adhesives to tissue within a human or animal.

BACKGROUND OF THE INVENTION

Percutaneously accessing major vascular structures is a key step in a variety of diagnostic and therapeutic procedures, including Percutaneous Transluminal Coronary Angioplasty (PTCA), Percutaneous Coronary Angiography and Percutaneous Coronary Atherectomy. After the procedure is completed, the instruments used to perform the procedure are withdrawn from the vessel leaving a potential source of bleeding.

The most common method used to prevent post-procedure bleeding at the access site involves the application of direct pressure to the perforation site until normal physiologic pathways have sealed the access site. There are several problems with this method. First, the pressure application technique may fail to prevent hemorrhage. Such a hemorrhage may be life-threatening hemorrhage or lead to a large hematoma. A large hematoma in the groin, for instance, may compromise the major nerve supply to the anterior lower extremity.

Secondly, the pressure application technique extends the length of the in-hospital stay. For example, a PTCA may be completed in 2 to 3 hours, but the patient will typically be hospitalized for several additional hours or overnight, simply to allow the access site to seal physiologically. During this extended hospital stay the patient is required to stay immobile, often with a sand bag taped to his thigh (in the case of femoral artery access).

More than 500,000 PTCAs were performed worldwide in 1992 (Cowen Report, March 1993), as well as several times that number of other procedures requiring accessing major vascular structures percutaneously. Thus, the increased length of in-hospital stay necessitated by the pressure application technique considerably increases the expense of procedures requiring such vascular access.

A technique that would allow faster and safer sealing of a vascular access site would save a significant amount of health care resources. There remains a need for such a technique.

SUMMARY OF THE INVENTION

In one aspect, the present invention provides a method of percutaneous transluminal coronary angioplasty and inhibiting arterial bleeding at the arterial perforation site following the procedure which includes the steps of performing the procedure, temporarily inhibiting blood flow through the vessel, exposing the vessel wall surrounding the perforation and applying a tissue adhesive to the vessel wall surrounding the perforation to seal the perforation.

In another aspect, the present invention provides a method of closing a vascular perforation of the type produced during percutaneous transluminal catheterization procedures which includes the steps of exposing the vessel wall surrounding the perforation and applying a tissue adhesive to the surface of the wall surrounding the perforation to seal the perforation.

Further, the invention provides an applicator suitable for percutaneously delivering a tissue adhesive to the surface of a perforated vascular wall and other uses. The applicator includes a tubular housing having a proximal control end of various configurations, a distal delivery end with a delivery surface having a diameter larger than the perforation and a reservoir containing expressible tissue adhesive.

BRIEF DESCRIPTION OF THE DRAWINGS

FIG. 1 is a cross-sectional elevational view of an applicator embodying features of the invention.

FIG. 2 is a schematic view of a step in one method of use of the invention.

FIG. 3 is a schematic view a step in one method of use of the invention that occurs later than the step shown in FIG. 2.

DETAILED DESCRIPTION OF PREFERRED EMBODIMENTS

Figure 4:
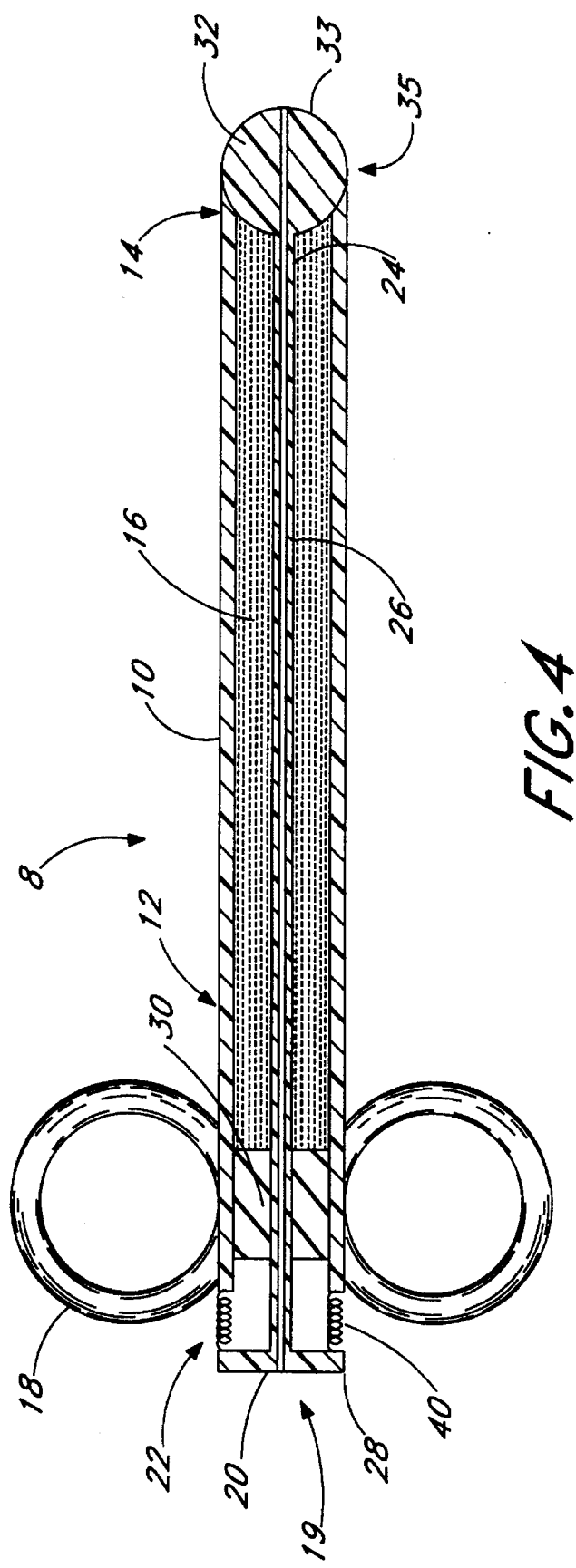
FIG. 4 is a cross-sectional elevational view of an alternative embodiment of an applicator embodying features of the invention.

As discussed above, there is a need for a technique which will seal a vascular perforation created during a variety of commonly performed diagnostic and therapeutic procedures, including for example, Percutaneous Transluminal Coronary Angioplasty (PTCA), Percutaneous Coronary Angiography and Percutaneous Coronary Atherectomy. In addition, the device and method may have applications in the emergency treatment of trauma, wound closure following surgical procedures and the like. For convenience, the present disclosure will consider primarily the vascular perforation application.

An ideal technique would seal the perforation rapidly, cost effectively and permanently. If used to close a femoral or brachial artery, the technique should result in a seal that can withstand the uppermost potential limits of systolic blood pressure (around 300 mmHg) found in those vessels and the seal should be put in place with an absence of or no more than minimal enlargement of the original percutaneous entrance. One aspect of the present invention addresses the problems inherent in closing a perforation in a femoral or brachial artery following left heart or coronary artery catheterization by providing a device and a method that can be used to create a rapid and permanent seal.

Referring to FIG. 1, there is illustrated one embodiment of the invention for delivering a tissue adhesive to a bodily surface. For convenience, tissue adhesive will be discussed herein, although any of a wide variety of other fluids or fluid-like media can be delivered utilizing the applicator of the present invention. The apparatus of the present invention can also be utilized to deliver materials to any of a wide variety of structures, as will be apparent to one of skill in the art. The present disclosure will discuss embodiments primarily intended for delivery to tissue of the type which covers or surrounds a lumen, cavity or organ, or potential lumen or cavity, within a human or other animal.

The illustrated embodiment comprises an applicator 8 having a generally tubular housing 10 with a proximal control end 12, a distal delivery end 14 and a reservoir 16. Located near the proximal control end 12 are gripping structures, such as a pair of rings 18 to improve the ease of grasping the applicator 8.

A control 19 is provided near proximal end 12 for controllably expressing adhesive from the reservoir 16, as will be discussed. Any of a variety of control structures can be used, such as push buttons, levers, plungers and the like. In addition, a control in the form of a rotating knob may be provided, that functions such that rotation of the knob causes a measured amount of adhesive to be released onto the delivery surface by opening a valve, or consecutively opening and closing a valve, leading from the reservoir. Tactile, auditory or visual feedback or a combination of feedback may be provided as part of the knob control to alert the operator when the measured amount of adhesive has been expressed. Other types of controls will be apparent to one of skill in the art in view of the disclosure herein.

The illustrated control 19 comprises a spring loaded proximal end 22, a distal end 24 and a shaft 26. The proximal end 22 comprises a movable button 20 having a stop 28 of such dimensions or structures that its axial distal travel is limited by the proximal end 12 of the tubular housing 10.

The permissible axial travel of moveable button 20 is determined by the desired volume of adhesive to be expressed upon depression of the button 20. Preferably, the applicator 8 of the present invention is provided in a single unit dose delivery form, so that a single depression of button 20 or other control to its limit dispenses a single unit volume of adhesive, which has been predetermined at the point of manufacture for an intended application.

For example, in an embodiment of the applicator 8 for use following PTCA arterial perforations, a volume of generally no more than about 1.0 mm$^3$, and preferably no more than about 0.5 mm$^3$ adhesive will be desirably delivered. Other structures for limiting the delivered volume can be readily incorporated into the applicator 8 by one of skill in the art.

The control 19 is preferably linked to a moveable wall 30 in the reservoir 16. Manipulation of the control 19 advances moveable wall 30 in a manner that reduces the volume of the reservoir 16, thereby expressing contents of the reservoir by way of the applicator 32. Moveable wall 30 may comprise a moveable diaphragm, other flexible wall, slidable piston, as illustrated in FIG. 1, or other structure for expressing contents from reservoir 16 in response to manipulation of control 19.

In the illustrated embodiment, adhesive is expressed from the reservoir 16 by way of a valved opening 35 for providing valved fluid communication between the reservoir and the delivery surface 33. Conveniently, the same axial distal motion produced by depression of button 20 both displaces moveable wall 30 and opens the valve 35 to permit escape of adhesive therethrough.

In this embodiment, the applicator 32 comprises a generally radially symmetrical structure, such as a sphere. The proximal portion of this sphere seats within or against the distal end 14 of tubular body 10, to enclose the reservoir 16 therein. Preferably, a biasing means, such as a spring 40, is provided for biasing the valve 35 in the closed position. Alternative biasing means can also be used, such as polymeric springs and structures which utilize the elastic deformation properties of a plastic material.

Depression of button 20 unseats the applicator 32 from the distal end 14 of housing 10, to provide an annular flow path around applicator 32. Adhesive expressed through valve 35 travels around the applicator 32 to coat a delivery surface 33 generally on the distal portion thereof.

The delivery surface 33 on applicator can take any of a variety of forms. Optimally, the delivery surface 33 facilitates the application of a substantially uniform coat or layer of adhesive over an area that is larger than the arterial perforation site. In general, forms of delivery surface 33 which reduce the risk of any traumatic injury to the tissue are preferred, such as spherical, or other rounded, blunt tips. A relatively flat distal delivery surface 33 can also be utilized, as will be apparent to one of skill in the art. Alternatively, delivery surface 33 comprises an absorptive blotter material, a permeable membrane or other microporous structure for permitting expression of adhesive directly therethrough.

In general, it is desired that the delivery surface 33 be sufficiently sized relative to the perforation of the vessel wall that the delivery surface 33 will not be penetrable through the perforation unless excessive distal force is applied. In a typical PTCA procedure, the natural elasticity of a major artery wall will normally cause the perforation 60 to shrink to about 30% of its original area, upon removal of the procedure instrumentation. This natural shrinkage leaves a vessel wall perforation approximately 1 mm in diameter. For the purposes of the present invention, therefore, an applicator 8 having a delivery surface 33 with a diameter of at least about 2 mm and preferably a delivery surface of about 3 mm will be utilized.

With this structure, the operator can readily determine through tactile feedback when the delivery surface 33 is securely placed in contact with the vessel wall, yet the risk of perforation through the vessel wall is minimized. This reduces the likelihood that the delivery surface 33 will be introduced into the vessel, which could undesirably introduce adhesive into the bloodstream.

In addition to or as an alternative to reliance upon the size of the delivery surface 33 for limiting distal travel of the applicator 8, other structures, such as distally extending locating pins, radio opaque markers, and the like, can be incorporated into the applicator 8 of the present invention.

The distal end 14 of the applicator 8 is preferably configured in a manner that minimizes or prevents any contact between the delivery surface 33 and the tissue through which the delivery surface 33 must travel en route to the perforation 60 on the vessel wall. In one embodiment, this is accomplished by introducing the applicator 8 through a tubular introduction cannula 50, as is illustrated in FIG. 3 and will be described infra. In general, the cannula 50 has a sufficient interior diameter to accept the applicator 8, yet a sufficiently small exterior diameter to permit convenient penetration up to the perforated vessel wall.

Preferably, the distal end 54 of the cannula 50 exposes both the perforation 60 and a sufficient area of adjacent vessel wall surrounding the perforation 60 so that a sufficient volume of adhesive can be delivered from delivery surface 33 to the vessel wall. For a typical PTCA arterial perforation 60, having a diameter of about 1 mm, an introduction cannula 50 having an inside diameter of about 3 mm and an outside diameter of about 4 mm at its distal end 54 may conveniently be used.

Alternatively, the function of introduction cannula 50 can be readily accomplished by a structure integrally formed or secured to the applicator 8. For example, the delivery surface 33 can be retractably disposed within an outer tubular housing, as will be readily appreciated by one of skill in the art in view of the disclosure herein. As is illustrated in FIG. 2, the distal end of the cannula 50 or other introduction structure is preferably inclined in a manner that permits uniform contact to the vessel wall while the longitudinal axis of the applicator 8 is inclined at an angle to the vessel wall, which approximates the typical entry angle for the percutaneous perforation.

The reservoir 16 contains any of a variety of tissue adhesives. Suitable adhesives for in vivo use include adhesives within the cyanoacrylate family. In one preferred embodiment, the tissue adhesive comprises one or more of methyl cyanoacrylate, ethyl cyanoacrylate, n-propyl cyanoacrylate, isopropyl cyanoacrylate, n-butyl cyanoacrylate, isobutyl cyanoacrylate, n-amyl cyanoacrylate, isoamyl cyanoacrylate, 3-acetoxypropyl cyanoacrylate, 2-methoxypropyl cyanoacrylate, 3-chloropropyl cyanoacrylate, benzyl cyanoacrylate, phenyl cyanoacrylate, alkenyl cyanoacrylate, butyl-2-cyanoacrylate, alkoxyalky 2-cyanoacrylates or fluorinated 2-cyanoacrylates or combinations, thereof. More preferably, the tissue adhesive comprises ethyl cyanoacrylate or butyl-2-cyanoacrylate. These latter two compounds, available from Loctite Corporation (Hartford, Conn.), are normally in a liquid state with water-like viscosity. They harden almost instantaneously upon exposure to atmospheric humidity. Therefore, the reservoir 16 is provided with moisture-tight proximal and distal ends formed by the moveable wall 30 and the proximal end of the applicator 32, to maintain the tissue adhesive in liquid state prior to expression. Preferably, the device is also produced under low humidity conditions and stored in a desiccated package. A removable distal cap (not illustrated) may also be used.

Cyanoacrylate adhesives have been found to harden relatively rapidly when stored below a critical volume of adhesive. Hence, if cyanoacrylate is used, it will be preferable for the reservoir 16 to contain more adhesive than is necessary to seal a typical vascular access site. Preferably, a reservoir volume of at least about 1 to 2 gm is provided to maintain the cyanoacrylate in liquid form in the applicator prior to use. The total volume of adhesive, the desiccation measures and sealing structures on the reservoir 16 can be optimized to produce a desired shelf life by one of skill in the art in view of the disclosure herein.

When used to seal an in vivo tissue surface, cyanoacrylates have several particular advantages. First, they harden almost instantaneously on contact, because of the moisture content of most tissues. For example, they will harden when placed on living vascular walls, and endothelial and mesothelial surfaces. Second, experiments by the inventor indicate that cyanoacrylate sealed vascular punctures can withstand several times the maximum potential systolic pressure, and hence, would not be expected to fail when used to seal a perforation on a vascular wall. Also, cyanoacrylates are naturally thrombogenic. This is an advantage in sealing vascular walls as it promotes the first step in healing the wall. Further, because it seals so rapidly, the risk of embolization or migration can be minimized through the use of the applicators disclosed herein.

Various compounds may be added to the cyanoacrylates to alter the properties of the adhesive. For example, polyacrylic acid having a molecular weight of 200,000 to 600,000 may be cross-linked to the cyanoacrylate to form a suitable biocompatible material. These combination compounds allow the absorbability and resorption rate to be coordinated with the tissue regeneration rate and feature higher elasticity than cyanoacrylates alone. Other additives, such as stabilizers, viscosity modifiers and medications can also be included as desired.

In another aspect of the present invention, there is provided a method for delivering a tissue adhesive to a surface which covers or surrounds a lumen, cavity or organ, or potential lumen or cavity, within a human or animal. In one preferred embodiment, the method comprises the steps of providing an applicator having an atraumatic delivery surface, a reservoir and a control for expressing media from the reservoir to the delivery surface.

The delivery surface is placed near or in contact with the tissue surface surrounding an opening therein, and the control is activated to express tissue adhesive from the reservoir to the delivery surface. The delivery surface is thereafter brought into contact or maintained in contact with the vessel wall to deliver a layer of adhesive to the vessel wall. These basic steps are discussed in greater detail below.

This method can be used to close any exposed surface which can be reached by the applicator 8. For example, it has uses in open laparotomy for closing the peritoneal surfaces of the various hollow viscera, diaphragm and omentum. It has potential in sealing the surface of liver and spleen to prevent intraperitoneal hemorrhages. Further, it can be used to seal lung, heart and pleura, as after traumatic, iatrogenic or disease induced perforation.

In another aspect of the present invention, a method is provided for inhibiting arterial bleeding at the arterial access site after Percutaneous Transluminal Coronary Angioplasty (PTCA), Percutaneous Coronary Angiography, Percutaneous Coronary Atherectomy and similar procedures. In this method, access into an artery such as the femoral or brachial is made percutaneously in a manner well known to those with skill in the art. At the conclusion of the procedure, the catheter is withdrawn and pressure applied proximal to the access site to inhibit bleeding. The applicator 8, as in one embodiment described above, is advanced through the skin entrance site until the delivery end 14 contacts the vascular perforation 60 and a portion surrounding vascular wall 70. Tissue adhesive is expressed from the delivery end 14 of the applicator 8 and allowed to harden over the perforated tissue, sealing the opening. The applicator 8 is withdrawn and the skin entrance dressed in a usual manner.

Another preferred embodiment of a method for inhibiting arterial bleeding at the arterial access site after left heart or coronary artery catheterization comprises the additional step of positioning the canula 50 over vascularly indwelling instrumentation, as described below. Before describing this method, a summary of a representative intravascular surgical procedure utilizing a percutaneous opening will be given to further understanding of the invention.

In a representative procedure, an introduction needle is inserted percutaneously into a vascular structure, for example, the femoral artery. A guidewire is passed through the introduction needle to a desired site and the needle is withdrawn leaving the guidewire in position. Next, first and second sheaths, usually an introducer sheath and a dilator sheath, are passed over the guidewire and inserted into the vascular structure. The guidewire and first sheath are removed leaving the second sheath in place. Then the catheter or other instrumentation is inserted through the second sheath and threaded to a desired location, such as an atherosclerotic plaque.

Once the intravascular procedure has been completed, the catheter is removed. The usual method of hemostasis involves also removing the second sheath and applying pressure to the perforation site through the skin until hemostasis has occurred. However, an obturator may be inserted into the second sheath and both obturator and second sheath left in place for a period of time, prior to their removal. This additional step depends on the type of procedure and the patient's state of coagulation among other variables.

Referring now to FIG. 2 and FIG. 3, one embodiment of the present invention in illustrated. A canula 50, of the present invention, has a proximal end 52, a distal end 54 and a minimum inner dimension 56 greater than the maximum dimension of the perforation 60. Further, the canula 50 has a minimum inner dimension 56, at the proximal end 54 at least, that is greater than the maximum external dimension 38 of the tubular housing 10. This feature allows the applicator to axially movably fit within the cannula 50. The cannula 50 may have a smaller inner dimension (not shown) at the distal end 54 than at the proximal end 52 to facilitate placement of the catheter through the skin tract. In this latter embodiment, the inner dimension of the distal end is still large enough to allow the delivery surface 33 of the applicator 8 to contact the portion of the vascular wall 70 surrounding the perforation.

After completing the intravascular surgical procedure, the catheter (not shown) is withdrawn. A guidewire, 80 is placed through the second sheath (not shown) and the second sheath is withdrawn. External pressure is applied proximal (upstream) to the perforation as needed to control bleeding.

The cannula 50 is inserted over the guidewire 80 until the operator obtains tactile feedback that the cannula 50 has contracted the vascular wall 70. FIG. 2 illustrates the placement of the cannula 50 over the guidewire at the point where the cannula contacts the portion of the vascular wall 70 surrounding the perforation.

The guidewire 80 is removed leaving the cannula 50 in position over the perforation 60. Next, the applicator 8 is inserted through the cannula 50 until the delivery surface 33 contacts the vascular wall 70, without penetrating the perforation 60 into the vessel lumen 72. Again the operator will receive tactile feedback indicating that the delivery surface 33 has contacted the vascular wall 70. This step is shown in FIG. 3. Finally, an aliquot of tissue adhesive is expressed from the distal end 33 of the applicator 8, sealing the perforation 60. Both cannula 50 and applicator 8 are withdrawn from the body and a suitable dressing applied. Alternately, the cannula 50 can be withdrawn prior to discharging an aliquot of tissue adhesive.

Cyanoacrylate tissue adhesives will harden virtually on contact, and create a permanent seal. The operator may prefer to express tissue adhesive while the delivery surface 33 is spaced slightly apart from the tissue to be sealed. This permits the adhesive to flow over the delivery surface 33 and produce a relatively uniform coating for application to the target tissue.

Other embodiments will be readily apparent to those with skill in the art. For example, in addition to the above embodiment, the cannula 50 could be introduced over the catheter directly in procedures where the second sheath is withdrawn prior to the catheter. In another embodiment, a guidewire 80 is inserted prior to the withdrawal of the catheter, either through the catheter or between the catheter and the second sheath. The catheter and second sheath would be withdrawn leaving the guidewire and the cannula 50 would be placed as described above. In still another embodiment, the cannula 50 could be introduced over the second sheath rather than through the second sheath.

In yet another embodiment, the guidewire 80 is inserted into the perforation at the conclusion of the procedure. The instrumentation, other than the guidewire 80, is removed. An applicator with a central axially guidewire lumen 85 (FIG. 4) may then be threaded directly over the guidewire 80 until the distal end of the applicator contacts the portion of the vessel wall surrounding the perforation. The guidewire 80 is then removed and tissue adhesive is controllably expressed to seal the perforation. Finally, the applicator is removed and a suitable dressing applied.

In all cases, bleeding from the perforation site is preferably controlled by applying external pressure proximal (upstream) to the perforation. As described above, the natural elasticity of the vessel wall will normally cause the perforation to shrink, assisting in hemostasis.

Although the present invention has been described in terms of certain preferred embodiments, other embodiments can be readily devised by one with skill in the art in view of the foregoing, which will also use the basic concepts of the present invention. Accordingly, the scope of the present invention is to be defined by reference to the attached claims.

I claim:

1. A device for percutaneously delivering a tissue adhesive to a surface of a vascular wall surrounding a perforation in the vascular wall, comprising:

a tubular housing having a proximal control end and a distal delivery end;

a reservoir in the housing for containing a volume of tissue adhesive;

an applicator on the distal delivery end of the housing, said applicator further comprising a guidewire lumen extending axially therethrough; and a control on the proximal control end of the housing for controllably expressing adhesive from the reservoir to the applicator;

wherein said applicator comprises at least one, substantially smooth, atraumatic delivery surface facing in the distal direction in fluid communication with the reservoir for applying tissue adhesive to the surface of the vascular wall surrounding the perforation in the vascular wall.

2. A device as in claim 1, further comprising a piston in the reservoir for expressing tissue adhesive from the reservoir to the applicator.

3. A device as in claim 2, further comprising a stop for limiting the travel of the piston, to set a predetermined maximum delivered volume of tissue adhesive.

4. A device as in claim 1, further comprising a valve disposed in the flow path between the reservoir and the delivery surface, for sealingly retaining the tissue adhesive within the reservoir.

5. A device as in claim 4, wherein said control comprises an actuator on the proximal control end for simultaneously opening the valve and expressing tissue adhesive from the reservoir to the delivery surface.

6. A device as in claim 1, further comprising an introduction cannula, axially movably disposed about the applicator, for providing access to a portion of the vascular wall including the perforation.

7. A device as in claim 1 further comprising a tissue adhesive in the reservoir, wherein the tissue adhesive is selected from the group consisting of methyl cyanoacrylate, ethyl cyanoacrylate, n-propyl cyanoacrylate, isopropyl cyanoacrylate, n-butyl cyanoacrylate, isobutyl cyanoacrylate, n-amyl cyanoacrylate, isoamyl cyanoacrylate, 3-acetoxypropyl cyanoacrylate, 2-methoxypropyl cyanoacrylate, 3-chloropropyl cyanoacrylate, benzyl cyanoacrylate, phenyl cyanoacrylate, alkenyl cyanoacrylate, butyl- 2-cyanoacrylate, alkoxyalky 2-cyanoacrylates, fluorinated 2-cyanoacrylates and combinations thereof.

8. A device as in claim 7, wherein the tissue adhesive comprises a cyanoacrylate selected from the group consisting of ethyl cyanoacrylate and butyl-2-cyanoacrylate.

* * * * *